US012642527B2

(12) United States Patent
Jain

(10) Patent No.: US 12,642,527 B2
(45) Date of Patent: Jun. 2, 2026

(54) RECIRCULATING DISTAL INTESTINAL CONTENT

(71) Applicant: Saint Louis University, St. Louis, MO (US)

(72) Inventor: Ajay Kumar Jain, St. Louis, MO (US)

(73) Assignee: Saint Louis University, St. Louis, MO (US)

( * ) Notice: Subject to any disclaimer, the term of this patent is extended or adjusted under 35 U.S.C. 154(b) by 302 days.

(21) Appl. No.: 18/480,631

(22) Filed: Oct. 4, 2023

(65) Prior Publication Data

US 2024/0115264 A1 Apr. 11, 2024

Related U.S. Application Data

(60) Provisional application No. 63/413,988, filed on Oct. 7, 2022.

(51) Int. Cl.
*A61B 17/11* (2006.01)
*A61F 2/04* (2013.01)
*A61F 2/24* (2006.01)

(52) U.S. Cl.
CPC ........ *A61B 17/1114* (2013.01); *A61F 2/2496* (2013.01); *A61B 2017/1135* (2013.01); *A61F 2002/045* (2013.01)

(58) Field of Classification Search
CPC ........................................... A61B 17/11–1146
See application file for complete search history.

(56) References Cited

U.S. PATENT DOCUMENTS

| | | |
|---|---|---|
| 2009/0240339 A1 | 9/2009 | Teitelbaum et al. |
| 2019/0125474 A1 | 5/2019 | Luntz et al. |
| 2020/0390590 A1 | 12/2020 | O'Grady et al. |
| 2022/0061977 A1 | 3/2022 | Dunn et al. |

OTHER PUBLICATIONS

Davis; H et al. Intestinal Recirculation as an Aid to Absorption. A.M.A. Archives of Surgery, vol. 79, Oct. 1959, p. 597-599, [ retrieved on Sep. 29, 2025]. (Year: 1959).*
Redmond; D et al. Effects of Recirculating Jejunal Loops on Absorption and Transit After Massive Bowel Resection in Dogs. Surgical Forum, vol. 15, 1964, p. 291-292, [retrieved on Sep. 29, 2025]. (Year: 1964).*
Altman, D et al. Massive Intestinal Resection: Inadequacies of the Recirculating Loop. Surgical Forum, vol. 16, 1965, p. 365-366, [retrieved on Sep. 30, 2025]. (Year: 1965).*

(Continued)

*Primary Examiner* — Jessica Arble
*Assistant Examiner* — Linnae E. Raymond
(74) *Attorney, Agent, or Firm* — Brownstein Hyatt Farber Schreck, LLP

(57) ABSTRACT

A recirculation system for recirculating intestinal content within an intestinal tract of a subject including a recirculation pathway extending from a distal portion of the intestinal tract to a proximal portion of the intestinal tract forming a recirculation loop for recirculating the intestinal content through the proximal portion of the intestinal tract to increase nutrient absorption from the intestinal content. A bypass pathway in fluid communication with the recirculation pathway and configured to divert the intestinal content from the recirculation pathway to continue along the intestinal tract.

3 Claims, 10 Drawing Sheets

(56)          References Cited

OTHER PUBLICATIONS

Mackby; M et al. Methods of Increasing the Efficiency of Residual Small Bowel Segments. American Journal of Surgery, vol. 109, Jan. 1965, p. 32-38, [retrieved on Sep. 29, 2025]. (Year: 1965).*

Budding; J et al. Role of Recirculating Loops in the Management of Massive Resection of the Small Intestine. Surgery, Gynecology, and Obstetrics, vol. 125, No. 2, Aug. 1967, p. 243-249, [retrieved on Sep. 29, 2025]. (Year: 1967).*

Diego; M et al. Short-Gut Syndrome. Archives of Surgery, vol. 117, Jun. 1982, p. 789-795, [retrieved on Sep. 29, 2025]. (Year: 1982).*

Hutchinson; C et al. Autologous Internal Recirculation of Distal Intestinal Content Mitigated Liver and Gut Injury in a Novel Piglet Short Bowel Syndrome Model. Gastroenterology, vol. 162, No. 7, May 2022, S-180, [retrieved on Sep. 29, 2025]. (Year: 2022).*

Soop; M et al. Surgery for Patients with a Short Bowel and Tissue Engineering. Intestinal Failure [online]. Springer, 2023, [retrieved on Sep. 29, 2025]. (Year: 2023).*

Carter, B.A., et al., "Mechanisms of Disease: Update on the Molecular Etiology and Fundamentals of Parenteral Nutrition Associated Cholestasis," 2007, Nature, 4:277-28. Abstract Only.

Jain, A.K., et al., "Enteral Bile Acid Treatment Improves Perenteral Nutrition-Related Liver Disease and Intestinal Mucosal Atrophy in Neonatal Pigs," 2012, Am J Physiol, 301:G218-G224, 7 pages.

Nies, J.M., et al., "Fibroblast Growth Factor Signaling in Metabolic Regulation," 2016, Endocrinol (Lausanne), 6:193, 15 pages.

Zhao, L., "the Gut Microbiota and Obesity: from Correlation to Causality," 2013, Nat Rev Micro, 11:639-647. Abstract Only.

\* cited by examiner

EN: Piglets fed milk ad lib, no bowel resection
TPN: Piglets receiving only TPN, no bowel resection
SBS: Piglets receiving only TPN, 75% small bowel resection
SBS-O: Piglets receiving only TPN, 75% bowel resection with
end ostomy
RDIC-Loop-EN: Piglets receiving EN, 75% small bowel resection
with internal recirculation of distal intestinal contents

Linear Gut Mass - Proximal

RECIRCULATING DISTAL INTESTINAL CONTENT

CROSS-REFERENCE TO RELATED APPLICATION

This application claims priority to U.S. Provisional Patent Application Ser. No. 63/413,988, filed Oct. 7, 2022, and which is hereby incorporated by reference in its entirety.

STATEMENT REGARDING FEDERALLY SPONSORED RESEARCH OR DEVELOPMENT

This invention was made with government support under Grant Nos. RO1 DK131136 and R21 AI169487 from the National Institute of Health (NIH). Therefore, the government has certain rights in the invention.

FIELD

The present disclosure relates to recirculation of distal intestinal content. More specifically, the present disclosure relates to a system and process for recirculating distal intestinal content into the proximal small bowels of a subject for the treatment of short bowel syndrome (SBS).

BACKGROUND

Short bowel syndrome (SBS) is a condition in which the body is unable to absorb sufficient nutrients from foods eaten due to the shortened length of the small intestine. Maintenance of nutritional needs from regular enteral feeding is not possible for patients with SBS. Therefore, SBS patients require intravenous nutrition via total parenteral nutrition (TPN) for survival. If SBS patients do not receive TPN, the side effects of SBS can include intestinal failure associated liver disease (IFALD) and gut atrophy. However, there are long term complications associated with TPN. These complications include steatosis, cholestasis, cirrhosis, portal hypertension, and liver failure. In addition, gut mucosal atrophy and gut inflammation may still result in patients who undergo TPN. Thus, even with the current treatments, SBS patients have extensive morbidity and need intensive medical managements, with many such patients requiring a multi-visceral transplant for survival.

SUMMARY

In one aspect, a recirculation system for recirculating intestinal content within an intestinal tract of a subject generally comprises a recirculation pathway extending from a distal portion of the intestinal tract to a proximal portion of the intestinal tract forming a recirculation loop for recirculating the intestinal content through the proximal portion of the intestinal tract to increase nutrient absorption from the intestinal content. A bypass pathway is in fluid communication with the recirculation pathway and configured to divert the intestinal content from the recirculation pathway to continue along the intestinal tract.

In another aspect, a method of recirculating intestinal content in a subject's intestinal tract generally comprises directing intestinal content along a recirculation pathway extending from a distal portion of the intestinal tract to a proximal portion of the intestinal tract to increase nutrient absorption from the intestinal content. Diverting the intestinal content from the recirculation pathway along a bypass pathway in fluid communication with the recirculation pathway.

In yet another aspect, a surgical procedure for treating short bowel syndrome in a subject generally comprises creating am ostomy in an intestinal tract of the subject. Forming a first anastomosis between a distal portion of the intestinal tract and a proximal portion of the intestinal tract to create a recirculation loop for recirculating intestinal content through the proximal portion of the intestinal tract to increase nutrient absorption from the intestinal content. Forming a second anastomosis between the distal portion of the intestinal tract to a more distal portion of the intestinal tract to create a bypass pathway for diverting the intestinal content from the recirculation pathway to continue along the intestinal tract.

BRIEF DESCRIPTION OF THE DRAWINGS

Various embodiments of the presently disclosed recirculation system are described herein with reference to the drawings, wherein.

DETAILED DESCRIPTION OF EMBODIMENTS

Figure 1:
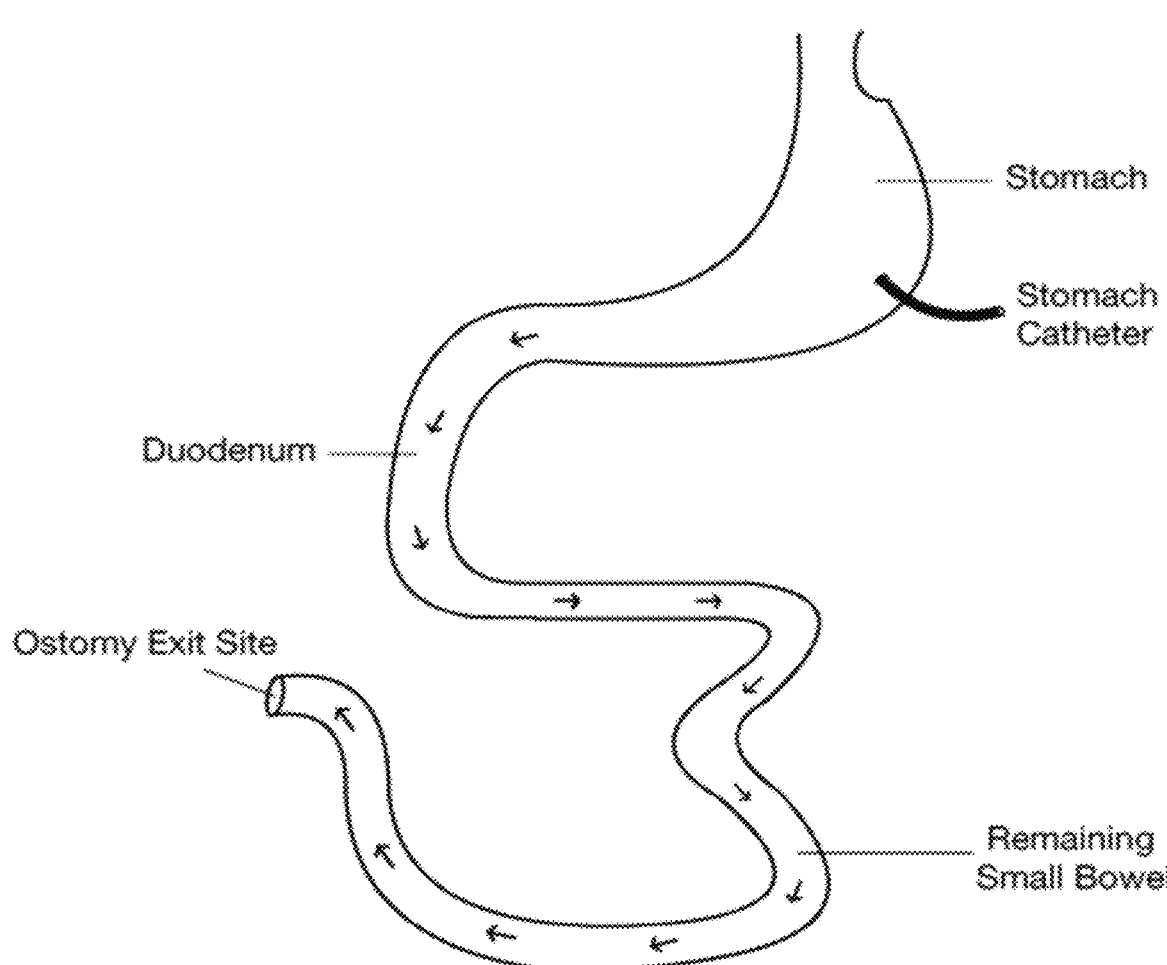
FIG. 1 is an illustration of a portion of a patient's digestive tract having short bowel syndrome where an ostomy has been created in the small intestine.
Figure 2:
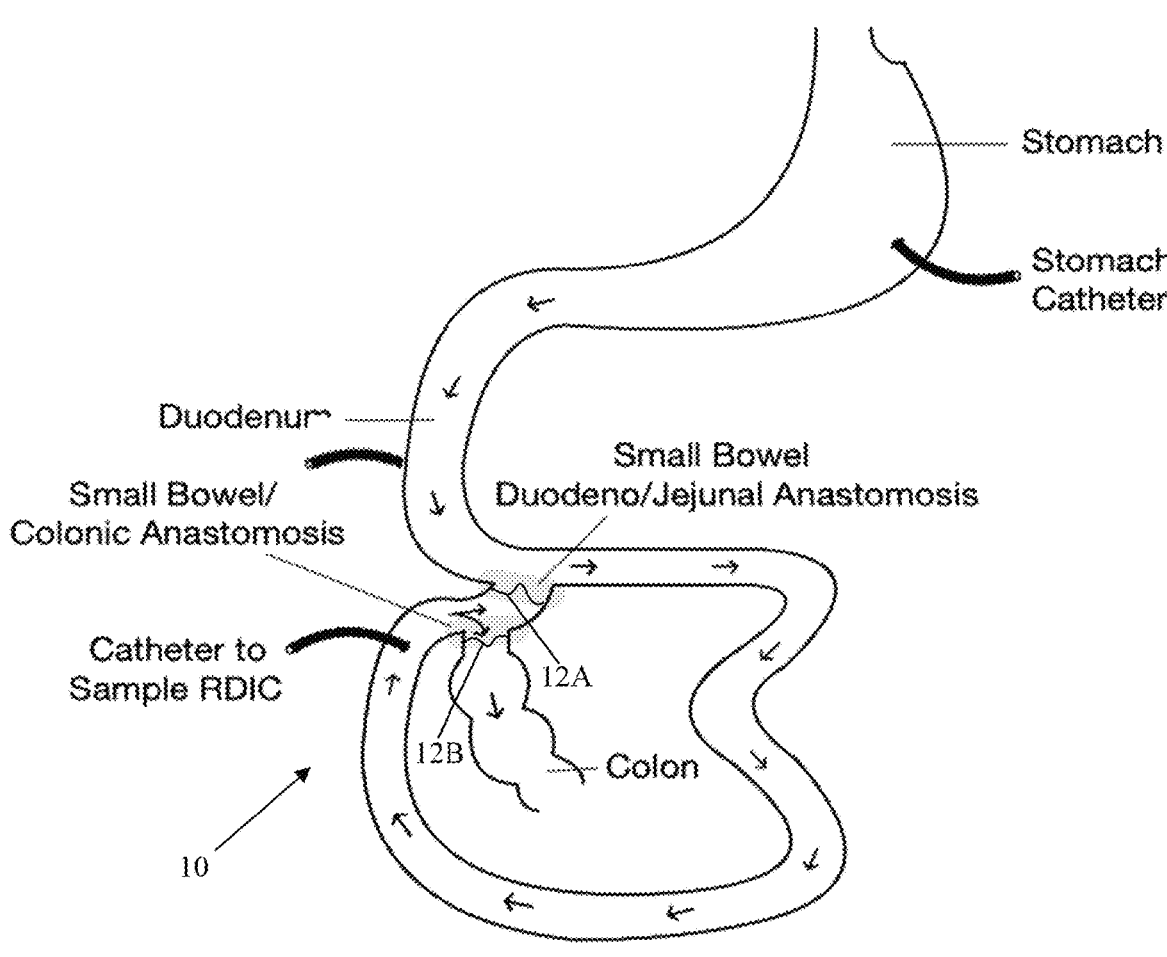
FIG. 2 is an illustration of a portion of a patient's digestive tract having short bowel syndrome where recirculation pathways have been created.

Referring to FIGS. 1 and 2, a procedure and system for recirculating distal intestinal content is illustrated. This procedure produces a fully internal (i.e., disposed completely within the subject's body) recirculation system 10 such that nutritional intestinal content can be recirculated through the subject's intestine to increase the subject's capacity to absorb the nutrients from the nutritional content into the intestine. This is particularly useful in individuals with short bowel syndrome (SBS) as the length of their small intestines is such that sufficient nutrient absorption is not possible along the natural length of their intestinal tract. In the illustrated embodiment, the recirculation system 10 is free of additional pumps, bags, or artificial passages used to facilitate recirculation of the intestinal content. However, the recirculation system 10 may include additional components, such as pumps, bags, catheters, tubing, etc., without departing from the scope of the disclosure.

A surgical procedure may be performed on a subject with SBS to configure their digestive tract for distal intestinal content recirculation in order to effectively increase the operational length of the subject's small intestine. In particular, the procedure may rearrange and reconfigure the pathways through the subject's intestine to produce at least one recirculation loop within the intestine so that nutritional content flowing through the shortened small intestine is able to flow from a distal location in the small intestine back to a proximal location in the small intestine, one or more times, to provide additional opportunities for absorption of the nutritional content. In the illustrated embodiment, this nutritional loop consists wholly of the small intestine and does not include any additional bags, pumps, or tubing connected to the small intestine. Thus, the potential for skin breakdown, bag leakage, and/or pump occlusion caused by an external system is eliminated in the disclosed system 10.

Referring to FIG. 1, an illustration of a portion of a patient's digestive tract is shown. In this illustration, the surgical procedure begins by creating an ostomy in the small intestine. While the large intestine (i.e., colon) is not shown in FIG. 1, it will be understood that the location of the ostomy may be at or near the junction between the small and large intestine. Thus, prior to the ostomy, the section of the small intestine shown in FIG. 1 will have been connected to the large intestine. The arrows in FIG. 1 indicate the natural path of the intestinal content flowing through the small intestine and into the large intestine. An optional stomach catheter is also shown in FIG. 1. The stomach catheter may be used for feeding directly to the stomach if feeding by mouth cannot be done.

Referring to FIG. 2, after creating the ostomy in the small intestine, the surgical procedure continues by creating an anastomosis between a distal end portion of the small intestine and a proximal portion of the small intestine. In the illustrated embodiment, the anastomosis is created between the duodenum and the jejunum (i.e., small bowel duodeno/jejunal anastomosis). For example, the site of the ostomy may be connected to a side wall of the duodenum. This operation functions to create a recirculation loop through the small intestine. The recirculation loop is illustrated by the circular pathway of arrows shown in FIG. 2. A length of the recirculation loop will depend on the length of the available small intestines. However, in one embodiment, the recirculation loop can be variable in length based on the underlying medical condition and anatomy. As previously discussed, this recirculation loop may be free of any additional tubing, bags, or pumps to facilitate recirculation. Rather, the recirculation loop is comprised entirely of the small intestine whereby the patient's body operates to automatically recirculate the intestinal content. In one embodiment, the recirculation loop defines a recirculation pathway whereby intestinal content is able to flow from a distal portion of the small intestine, through the anastomosis between the distal and proximal portions of the small intestine, back into the proximal portion of the small intestine for delivery back to the distal portion of the small intestine. Thus, nutritional content that may have otherwise been delivered directly to the large intestine is able to recirculate back through the small intestine. An optional intestinal catheter is shown attached to the distal section of the small intestine. This catheter may be used to sample the intestinal content to assess the efficacy of the recirculation loop. However, it will be understood that the intestinal catheter can be omitted.

Either before or after creating the anastomosis between the distal and proximal portions of the small intestine, an anastomosis can be created between the distal portion of the small intestine and the large intestine. For example, the proximal end of the large intestine that was disconnected from the distal end of the small intestine during the ostomy process can then be reconnected back to a distal side portion of the small intestine. In the illustrated embodiment, the anastomosis is created between the small bowels and the colon (i.e., small bowel/colonic anastomosis). Thus, in this embodiment, the anastomosis between the small intestine and the large intestine is located upstream from the anastomosis between the proximal and distal portions of the small intestine along the recirculation loop. Therefore, intestinal content recirculating through the small bowels will first pass the small bowel/colonic anastomosis before passing through the small bowl duodeno/jejunal anastomosis. In one embodiment, the anastomosis between the distal portion of the small intestine and the proximal end of the large intestine creates a bypass pathway whereby recirculated intestinal content can travel to the large intestine for further digestion.

Due to the nutrient rich nature of the intestinal content, and the design of the human digestive system, the body will direct the intestinal content through the recirculation loop (i.e., recirculation pathway), bypassing the large intestine, until the optimal amount of nutrients have been extracted from the intestinal content. For example, a section or chyme of intestinal content may recirculate through the recirculation several times to increase absorption. Once the nutrients have been extracted from the intestinal content and absorbed into the small intestine, the intestinal content will naturally flow into the large intestine along the bypass pathway. Thus, the recirculation procedure produces a physiologically powered and regulated recirculation system within the patient's body. As a result, adequate nutrient absorption is capable of being achieved in patients with short bowel syndrome.

In one embodiment, the recirculation system 10 includes at least one valve disposed along the recirculation loop for regulating the flow of nutritional content from the distal portion of the small intestine. The valve may comprise a non-artificial valve such as a mucosal valve. Still other types of valves are envisioned without departing from the scope of the disclosure. Referring to FIG. 2, a first valve 12A may be located generally at the anastomosis between the distal portion of the small intestine and the proximal portion of the small intestine. When the first valve 12A is open, nutritional content is allowed to flow from the distal portion of the small intestine into the proximal portion of the small intestine thereby recirculating the nutritional content through the small intestine. However, when the first valve 12A is closed, nutritional content is prevented from being recirculated through the small intestines. In this case, the nutritional content will be directed into the large intestines. The positioning of the first valve 12A is such that the opening and closing of the first valve may be controlled naturally by the subject's digestive system so that nutrient rich content is allowed to be recirculate through the small intestine prior to being delivered to the large intestine.

A second valve 12B may be provided at the anastomosis between the distal portion of the small intestines and the large intestine (i.e., colon). When the second valve 12B is open, nutritional content is allowed to flow from the distal portion of the small intestine into the large intestine thereby diverting the nutritional content away from the recirculation loop. However, when the second valve 12B is closed, nutritional content is prevented from entering the large intestines. In this case, the nutritional content will be directed into the proximal portion of the small intestine for recirculation through the small intestine. The positioning of the second valve 12B is such that the opening and closing of the second valve may be controlled naturally by the subject's digestive system so that nutrient poor content is allowed to pass into the large intestine.

Example

Figure 3:
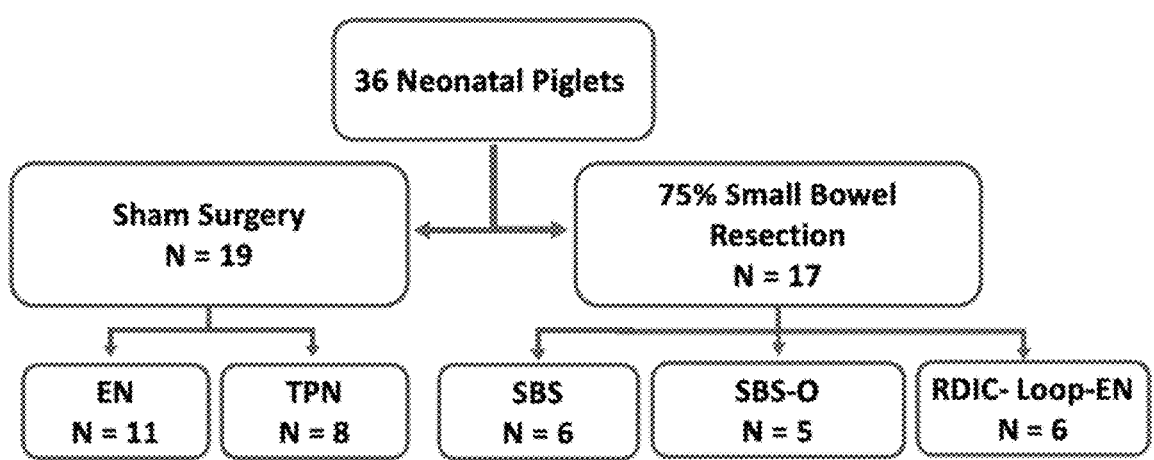
FIG. 3 is a schematic illustration of a study performed testing the process of recirculating distal intestinal content as compared to other conventional treatments for short bowel syndrome.

Referring to FIG. 3, a study was performed to test the efficacy of the recirculation system. In this study, 19 neonatal pigs were randomly allocated to receive enteral nutrition (EN) (n=11) or receive SBS and TPN (n=8) for approximately 2 weeks. To perform this study, an untethered ambulatory SBS piglet model was developed using miniature pumps, jugular, stomach and duodenal catheters, and surgical bowel resection closely replicating human SBS. The model allowed for gastric EN and cyclical recirculation of distal intestinal content into the proximal small bowel (RDIC) enabling delivery of full EN despite SBS. The SBS animals were further divided to get TPN only or RDIC. Liver, gut and serum were collected for histology, serum biochemistry, ELISA and western blot assays. Pairwise t-tests or Mann-Whitney U test were also conducted.

Figure 4A:
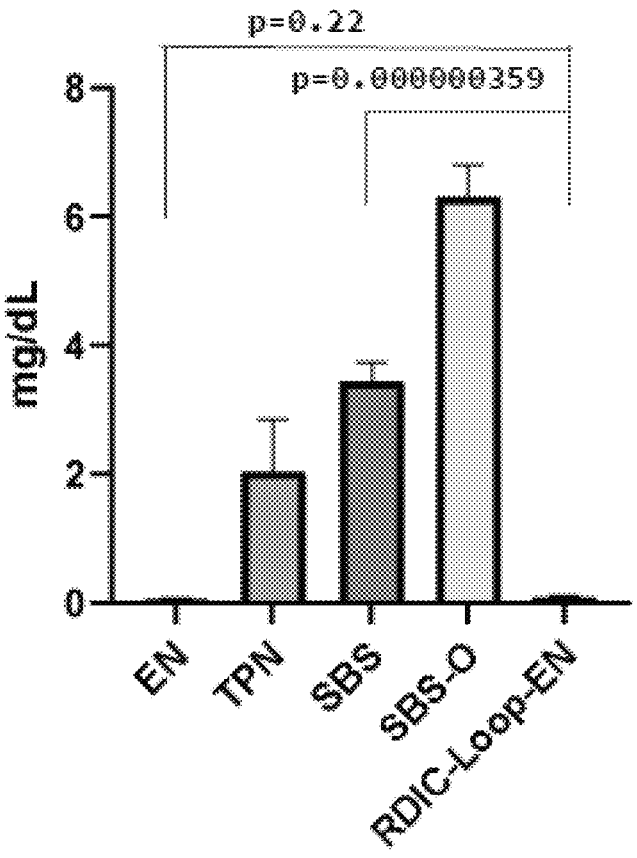
FIG. 4A is a graph of serum total bilirubin for each treatment protocol of the study.
Figure 4B:
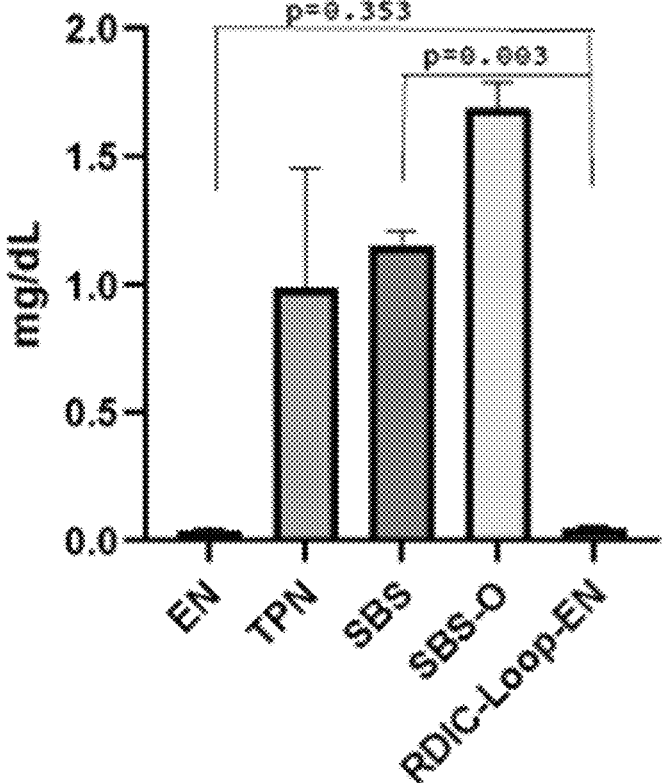
FIG. 4B is a graph of conjugated bilirubin for each treatment protocol of the study.
Figure 5A:
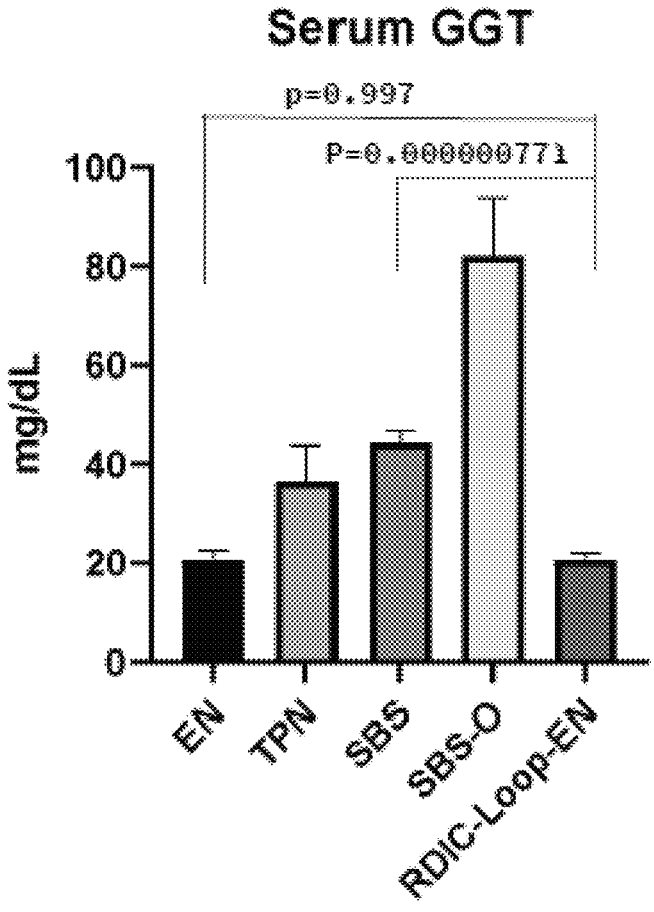
FIG. 5A is a graph of serum GGT for each treatment protocol of the study.
Figure 5B:
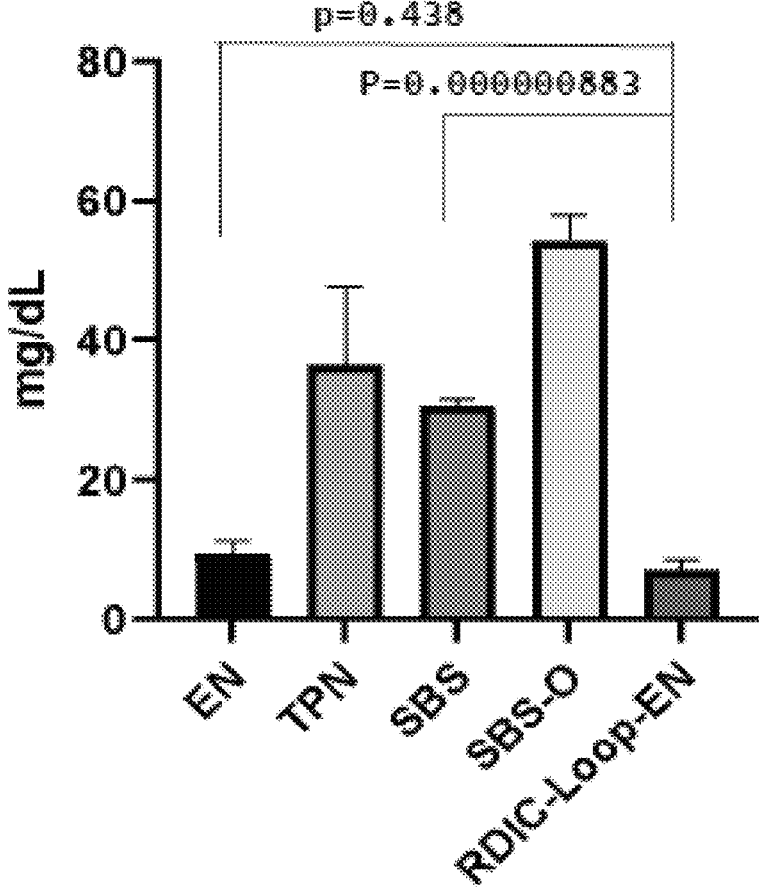
FIG. 5B is a graph of serum bile acids for each treatment protocol of the study.
Figure 6A:
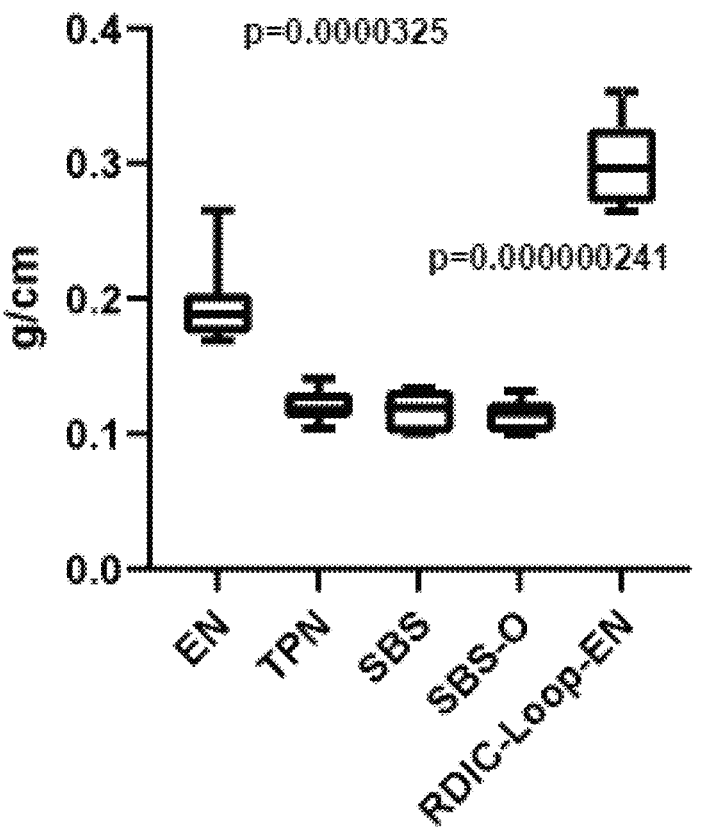
FIG. 6A is a graph of proximal linear gut mass for each treatment protocol of the study.
Figure 6B:
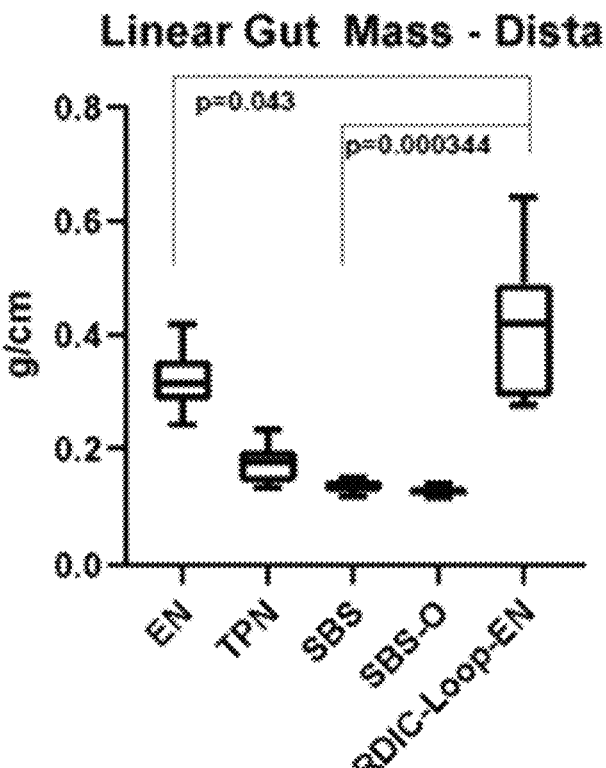
FIG. 6B is a graph of distal linear gut mass for each treatment protocol of the study.
Figure 7:
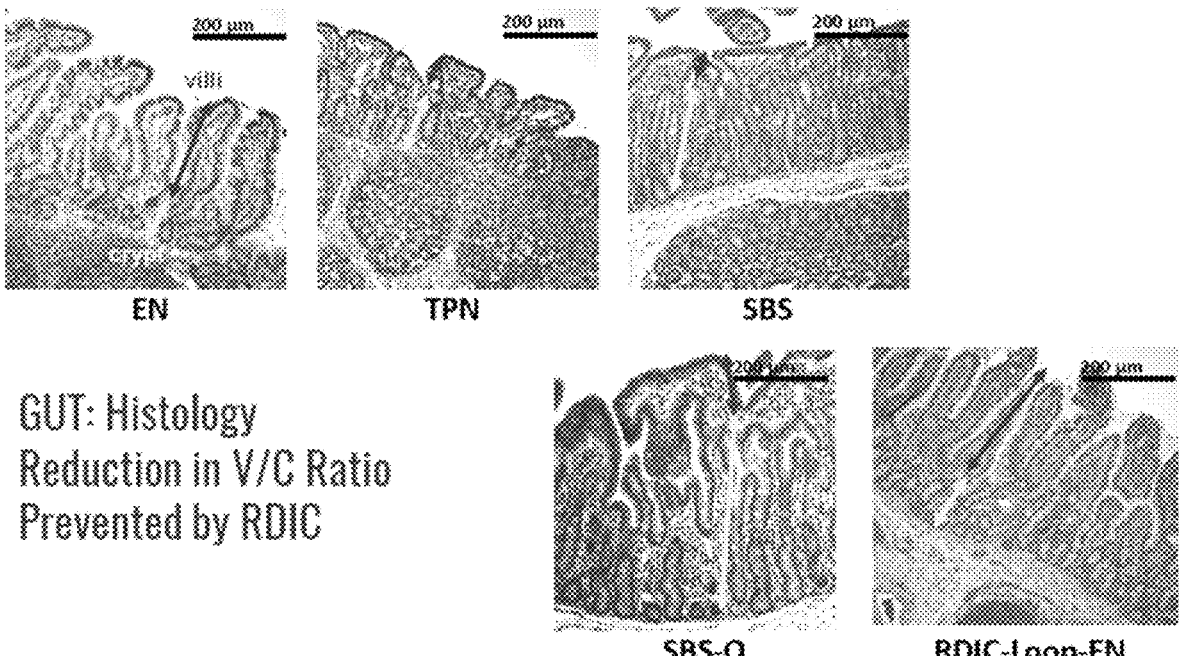
FIG. 7 are illustrations of histologies for each treatment protocol of the study.

The study found that piglets given TPN resulted in cholestatic liver injury while the piglets in the RDIC group had significantly reduced cholestasis markers compared to SBS. Referring to FIGS. 4A and 4B, the mean serum direct bilirubin for EN, SBS, and RDIC were 0.041 mg/dL, 1.13 mg/dL, and 0.052 mg/dL, respectively (p=0.003 for SBS vs RDIC, p=0.353 for EN vs RDIC). Thus, there was no statistically relevant elevation in bilirubin with the RDIC treated piglets. Referring to FIGS. 5A and 5B, the mean serum bile acids for EN, SBS, and RDIC were 9.46 mg/dL, 30.2 mg/dL, and 7.22 mg/dL, respectively. Finally, and with reference to FIGS. 6A and 6B, the mean GGT for EN, SBS, and RDIC were 20.8 U/L, 44.4 U/L, and 20.8 U/L, respectively. To evaluate gut growth, the lineal gut mass (LGM) was also measured. There was significant preservation in gut atrophy in RDIC animals. The mean proximal LGM for EN, SBS, and RDIC were 0.198 g/cm, 0.121 g/cm, and 0.300 g/cm, respectively (FIG. 6A). Likewise, the distal LGM for EN, SBS, and RDIC were 0.322 g/cm, 0.140 g/cm, and 0.417 g/cm, respectively (p=0.003 for SBS vs RDIC, p=0.136 for EN vs RDIC) (FIG. 6B). Finally, a study of the histology of the intestines showed a reduction in V/C ratio was prevented in the pigs that were treated with the recirculation system (RDIC). As shown in FIG. 7, the length of the intestinal villi for the subjects treated with the recirculation system was maintained at level consistent with the those treated with enteral nutrition (EN). Whereas, there was significant reduction in the villi length for the subjects that underwent TPN. Therefore, the study concluded that the recirculation system presents a novel method, which enables full EN delivery despite SBS.

Persons skilled in the art will understand that the systems and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical procedure for treating short bowel syndrome in a subject, the procedure comprising:
    creating an ostomy in an intestinal tract of the subject;
    forming a small bowel duodeno/jejunal anastomosis between a distal portion of the intestinal tract and a proximal portion of the intestinal tract to create a recirculation loop for recirculating intestinal content through the proximal portion of the intestinal tract to increase nutrient absorption from the intestinal content; and
    forming a small bowel/colonic anastomosis between the distal portion of the intestinal tract and a more distal portion of the intestinal tract to create a bypass pathway for diverting the intestinal content from the recirculation pathway to continue along the intestinal tract.

2. The procedure of claim 1, wherein the recirculation pathway extends from a distal portion of a small intestine of the subject to a proximal portion of the small intestine.

3. The procedure of claim 2, wherein the bypass pathway extends from the distal portion of the small intestine to a large intestine of the subject.

* * * * *